United States Patent [19]

Keve et al.

[11] Patent Number: 4,859,682
[45] Date of Patent: * Aug. 22, 1989

[54] 2-HALOGENATED-8- AND 1,8-SUBSTITUTED ERGOLENES

[75] Inventors: Tibor Keve; Gábor Megyeri; Stefkó Béla; Lajos Kovács, Jr.; Anna Kassai née Zieger, all of Budapest; Béla Kiss, Vecsés; István Laszlovszky, Budapest; Erzsébet Lapis, Budapest; Éva Pálosi, Budapest; Dóra Groó, Budapest; László Szporny, Budapest, all of Hungary

[73] Assignee: Richter Gedeon Vegyeszeti Gyar Rt., Budapest, Hungary

[ * ] Notice: The portion of the term of this patent subsequent to Jul. 21, 2004 has been disclaimed.

[21] Appl. No.: 40,938

[22] Filed: Apr. 21, 1987

[30] Foreign Application Priority Data

Apr. 25, 1986 [HU] Hungary ................ 1719/86

[51] Int. Cl.$^4$ .................. A61K 31/44; C07D 457/02
[52] U.S. Cl. ........................ 514/288; 546/67
[58] Field of Search ................ 546/67; 514/288

[56] References Cited

U.S. PATENT DOCUMENTS

| 3,992,385 | 11/1976 | Bach et al. | 546/67 |
| 4,348,391 | 9/1982 | Stutz et al. | 546/68 |
| 4,417,051 | 11/1983 | Sauer et al. | 546/69 |

FOREIGN PATENT DOCUMENTS

| 753635 | 1/1971 | Belgium | 546/67 |
| 82808 | 6/1983 | European Pat. Off. | 546/67 |
| 213850 | 3/1987 | European Pat. Off. | 546/67 |
| 3403067 | 8/1985 | Fed. Rep. of Germany | 546/67 |
| 3413657 | 10/1985 | Fed. Rep. of Germany | 546/67 |
| 237837 | 7/1986 | Fed. Rep. of Germany | 546/67 |

Primary Examiner—Donald G. Daus
Assistant Examiner—Cecilia Shen
Attorney, Agent, or Firm—Herbert Dubno; Jonathan Myers

[57] ABSTRACT

The invention relates to novel 2-halogenated 8- and 1,8-substituted ergolene derivatives of the formula (I) and the acid addition salts thereof, pharmaceutical compositions containing them and a process for their preparation. In the formula (I)

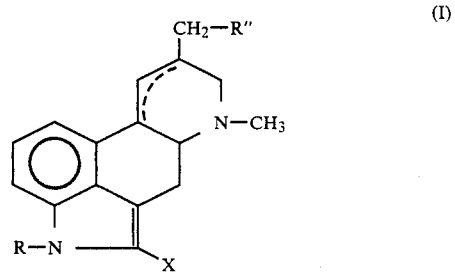

wherein
X stands for a halogen;
R stands for a $C_{1-4}$ alkyl group and
R″ means a hydroxyl group; or
R stands for an acyl or substituted acyl group and
R″ represents a halogen or an —OR' group, wherein R' stands for an acyl or substituted acyl group; or
R stands for hydrogen and
R″ means a halogen or an —OR' group, wherein R' stands for an acyl or substituted acyl group; and the dotted line means a double bond between the 8-9 or 9-10 positions.

The compounds of the formula (I) possess an antipsychotic and antihypoxic action and a negligable extrapyramidal side-effect.

6 Claims, No Drawings

2-HALOGENATED-8- AND 1,8-SUBSTITUTED ERGOLENES

The invention relates to novel 2-halogenated 8- and 1,8-substituted ergolene derivatives of the formula

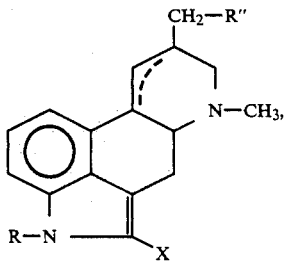

(I)

wherein
X stands for a halogen;
R stands for a $C_{1-4}$ alkyl group and
R" means a hydroxyl group; or
R stands for an acyl or substituted acyl group and
R" represents a halogen or an —OR' group, wherein R' stands for an acyl or substituted acyl group; and the dotted line means a double bond between the 8–9 or 9–10 positions, as well as their acid addition salts and pharmaceutical compositions containing these compounds.

According to another aspect of the invention, there is provided a process for the preparation of the compounds of the formula (I) and the acid addition salts thereof, which comprises
(a) alkylating a 2-halogenated ergolene derivative of the formula

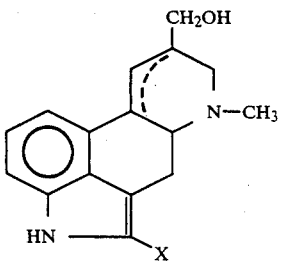

(II)

wherein X stands for a halogen, to obtain a compound of the formula (I) containing a $C_{1-4}$ alkyl group as R and a hydroxyl group as R"; or
(b)(i) diacylating a 2-halogenated ergolene derivative of the formula (II), wherein X stands for a halogen, with a carboxylic acid derivative suitable to acylate, or
(ii) monoacylating a 2-halogenated ergolene derivative of the formula (II), wherein X stands for a halogen, with a carboxylic acid or with a carboxylic acid derivative suitable to acylate and, after isolating, converting the thus-obtained monoacyl derivative of the formula (I), wherein
X is a halogen, R means hydrogen and R" stands for an —OR' group where R' stands for an acyl or substituted acyl group to a diacyl derivative by further acylating it with a carboxylic acid derivative suitable to acylate, or converting said monoacyl derivative of the formula (I) to a compound of the formula (I) containing a formyl group as R, to obtain compounds of the formula (I) containing an acyl or substituted acyl group as R and an —OR' group as R", wherein R' stands for an acyl or substituted acyl group; or (c)(i) formylating and simultaneously halogenating a 2-halogenated ergolene derivative of the formula (II), wherein X stands for a halogen, or
(ii) halogenating a 2-halogenated ergolene derivative of the formula (II), wherein X stands for a halogen and, after isolating, formylating the thus-obtained compound of the formula (I), wherein both X and R" stand for halogen and R means hydrogen, to obtain compounds of the formula (I) containing a formyl group as R and a halogen as R"; or
(d) isolating the monoacyl derivative obtained under (ii) in process (b) or the derivative obtained under (ii) in process (c) to obtain compounds of the general formula (I) containing hydrogen as R and a halogen or an —OR' group as R", wherein R' stands for an acyl or substituted acyl group, and, if desired, converting the compounds of the formula (I), obtained by using any one of the above processes, to their acid addition salts.

The compounds of the formula (I) of the invention are new and have valuable therapeutic action, particularly an antipsychotic and antihypoxic effect. Thus, the pharmaceutical compositions containing the compounds of the formula (I) or their acid addition salts as active ingredients as well as the process for the preparation of these pharmaceutical compositions are also within the scope of the invention.

In the above-defined formulae:
X as halogen may be chlorine, bromine or iodine;
R as a $C_{1-4}$ alkyl group may represent straight or branched chain groups such as a methyl, ethyl, n-propyl, isopropyl, n-butyl, secondary-butyl or tertiary-butyl group;
R as an acyl group may stand for an aliphatic acyl such as the formyl, acetyl, propionyl, butyryl or hexanoyl group; or an aromatic acyl such as the benzoyl or naphthoyl group; or an aralkylacyl such as the phenylacetyl or 3-phenylpropionyl group; or a heterocyclic acyl such as the picolyl, furoyl, nicotinoyl or isonicotinoyl group;
R as a substituted acyl group may represent a ring-substituted aromatic or heterocyclic acyl group such as a trimethoxybenzoyl, 4-chlorobenzoyl, 2-chlorobenzoyl or pyroglutamyl group;
R" as halogen may be chlorine, bromine or iodine;
R" as an —OR' group may contain an acyl or substituted acyl group as R', wherein R' may be one of the above-defined acyl groups for R.

The 2-halogenated ergolene derivatives, i.e. the 2-halolysergols(2-halo-8-hydroxymethyl-6-methyl-9-ergolenes) and the 2-haloelymoclavines(2-halo-8-hydroxymethyl-6-methyl-8-ergolenes), used as starting materials in the processes of the invention, are prepared by halogenating lysergol or elymoclavine, respectively, preferably as described hereinafter in Examples 1 to 4 and 6 to 8; or by isomerizing a 2-haloelymoclavine as described in Example 5. Lysergol(8-hydroxymethyl-6-methyl-9-ergolene) and elymoclavine(8-hydroxymethyl-6-methyl-8-ergolene) are known alkaloids of natural origin.

The antipsychotic and antihypoxic effect of the compounds of the formula (I) were proved by using the pharmacological tests described hereinafter.

The investigations were carried out on Hann-Wistar (LATI=a Hungarian firm with the name "Institute for Breeding Laboratory Animals") rats and CFLP (LATI)

mice. The compounds to be tested were orally administered in a volume of 5 ml/kg of body-weight (abbreviated: ml/kg) to rats and in a volume of 10 ml/kg to mice 60 minutes before starting the experiment.

The substances were suspended in a solution of Tween 80 of 0.5% strength and then diluted to the desired concentration with physiological saline solution.

The results are expressed as percentages or, alternatively the $ED_{50}$ values together with the 95% fiducial limits are given as calculated by means of the probit analysis [J. T. Litschfield and F. Wilcoxon: J. Pharmacol. 96, 99 (1949)].

Methods

1. Inhibition of the conditioned avoidance response (CAR inhibition)

The method of D. Bovet et al. (in: Neuropsychopharmacology Vol. 2., p. 142 ed. Elsevier Publishing House, Amsterdam, 1961) was used for this test.

Male rats weighing 140 to 160 g were conditioned for 10 days in an automated six-channel shuttle box (VKI). Each one session consisted of 30 cycles; the time of the partial cycles was 15 seconds for intersignal time, 15 seconds for light stimulus, 10 seconds for light stimulus and footshock (0.8 mA). The selected animals (n=6; selected on the basis of a performance higher than 80% at the 10th day) were treated with a 20 mg/kg dose of the compounds to be tested before the 11th session and their performance (i.e. the mean of the number of the conditioned avoidance responses) was compared to the value obtained for each group at the previous day taken as control value. The $ED_{50}$ values are summarized in Table 1.

2. Investigation of the cataleptogenic effect

The method of G. Stile and H. Launer [Arzneim.-Forsch. 21, 252 (1971)] was used for this test.

Male rats weighing 90 to 110 g (n=6) were treated with different doses of the compounds to be tested, then the number of the animals showing catalepsy was hourly observed for 5 hours. The upper limbs of the animals were placed onto a column of 7 cm in height and the animals were considered as cataleptic when they did not correct this particular posture for 30 seconds.

3. Investigation of the amphetamine group toxicity

The method of C. D. Proctor et al. [Arch. Int. Pharmacodyn. Ther. 163, 74 (1966)] was used for this test.

The examination was carried out on mice of both sexes weighing 22 to 27 g (n=5). At the 60th minute after administration of the compounds to be tested in a dose of 30 mg/kg, d-amphetamine in a dose of 21 mg/kg was intraperitoneally given to the animals tightly closed together (25 cm²/mouse) and the percentage of the perished animals was registered after 24 hours.

4. Investigation of the apomorphine hypothermia-reverting effect

The method of A. Barnett et al. [Arch. Int. Pharmacodyn. Ther. 198, 242 (1972)] was used for this test.

The rectal temperature of rats (n=5) was determined by using an Ellab thermometer before administering the compounds to be tested in a dose of 10 mg/kg. Thereafter, a dose of 5 mg/kg of apomorphine was intraperitoneally given and the temperature of the animals was hourly registered for 3 hours. The difference of the temperature change in °C. as related to the value obtained with only apomorphine is given in Table 1.

5. Investigation of the asphyxial anoxia

The method of C. Caillard et al. [Life Sci. 16, 1607 (1975)] was used for this test.

Mice (n=5) of both sexes weighing 22 to 24 g were starved for 16 hours, then treated with a 50 mg/kg dose of the compounds to be tested. After 60 minutes, the animals were placed in tightly closed glass bottles of 100 ml volume and the survival time was registered. Those animals were considered as protected, the survival time of which was found to be longer by 30% than that of the average survival time of the control group. The $ED_{50}$ values are summarized in Table 1.

As a reference drug, 2-bromolysuride, a known substance possessing strong neuroleptic effect (H. Watchel et al.: Life Sci., 33, 2583) was used.

Among the tested compounds of the invention, the following ones proved to be the most effective:

A: 1-Acetyl-8-acetyloxymethyl-2-chloro-6-methyl-9-ergolene;

B: 8-acetyloxymethyl-2-chloro-1-formyl-6-methyl-9-ergolene hydrogen sulfate

C: 2-chloro-8-chloromethyl-1-formyl-6-methyl-9-ergolene;

D: 1-acetyl-8-acetyloxymethyl-2-bromo-6-methyl-9-ergolene;

E: 2-chloro-1,6-dimethyl-8-hydroxymethyl-9-ergolene maleate.

TABLE 1

| Compound to be tested p.o. | CAR inhibition $ED_{50}$ mg/kg | Catalepsy $ED_{50}$ mg/kg | Ampetamine group tox. $ED_{50}$ mg/kg | Apomorphine hypothermia °C. 60 min | Apomorphine hypothermia °C. 120 min | Asphyxial anoxia $ED_{50}$ mg/kg |
|---|---|---|---|---|---|---|
| A | 3.4 | 46.5 | 19.6 | +1.3 | +1.3 | 34.8 |
| B | 3.7 | 51.9 | 10%* | +2.0 | +2.4 | 20%** |
| C | 12.9 | 0%ˣˣ | 0%* | +0.6 | +1.2 | 50%** |
| D | 4.6 | 42.4 | 0%* | +0.9 | +1.7 | 50%** |
| E | 24%ˣ | 0%ˣˣ | 0%* | +0.8 | +1.8 | 8.6 |
| 2-Bromolysuride | | 3.3 | | | | |

ˣ20 mg/kg p.o.
ˣˣ60 mg/kg p.o.
*30 mg/kg p.o.
**50 mg/kg p.o.

It is obvious from the results summarized in Table 1 that the strength and quality of the antipsychotic effect can be concluded from the inhibition of the conditioned avoidance response, whereas the expectable undesired effect can be judged from the dose causing catalepsy. In addition to the presumably strong antipsychotic action, the undesired extrapyramidal side-effect of the compounds of the invention only appears on administering doses which are about 14 times as high as the effective antipsychotic doses. This can be seen from the ratio between the cataleptogenic $ED_{50}$ and the condition avoidance response inhibiting $ED_{50}$.

It can be seen from the data of Table 1 that the amphetamine inhibiting effect of the compounds of the invention is practically negligible, in contradiction to the typical neuroleptics characterized by a significant amphetamine inhibiting action and extrapyramidal side-effects frequently occuring in the clinical practice.

The significant apomorphine-antagonizing action (reversion of the hypothermia) of the compounds is a proof of inhibition of the dopaminergic system.

In the case of the compound E containing a methyl group in 1-position, the antihypoxic effect comes into prominence as it can be seen from the data of Table 1.

Finally, when the compounds of the invention are compared to 2-bromolysuride on the basis of the method measuring the spontaneous catalepsy, it can be seen that the cataleptogenic doses of the compounds of the invention are much higher; thus, it can be expected that their undesired side-effect will be lower.

The processes of the invention are described hereinafter in detail.

According to process (a) of the invention, a 2-halogenated lysergol or 2-halogenated elymoclavine, respectively, of the formula (II), wherein X stands for chlorine, bromine or iodine, is alkylated at the 1-position of the ergolene skeleton. This alkylation can be carried out in a manner known per se, e.g. according to the following literature reference: Helv. Chim. Acta 40, 1727 (1957).

According to this method, the alkylation is transformed in liquid ammonia by using methyl iodide and metallic potassium at room temperature.

Alternatively, the alkylation may be carried out in a manner widely used for ergolene derivatives (c.f. the European patent specification No. 0,004,664), according to which a large excess of potassium hydroxide is suspended in anhydrous dimethylsulfoxide and then the ergolene derivative to be alkylated and the alkylating agent are added. An alkyl halide, preferably an alkyl iodide may be used as alkylating agent. The reaction is carried out at room temperature.

The reaction mixture is worked up by pouring it into water and filtering or extracting the product.

According to the variant (i) of the process (b) of the invention, a 2-halogenated lysergol or 2-halogenated elymoclavine, respectively, of the formula (II) is diacylated by using a carboxylic acid derivative suitable for acylating. The diacylation may be achieved by employing an acid anhydride, acyl halide or a ketene, preferably by using an acyl halide.

On using an acid anhydride for the diacylation, the reaction is carried out at a temperature higher than room temperature, preferably between 40° C. and the boiling point of the solvent. As solvent, an excess of the acid anhydride or a mixture of the acid anhydride with the corresponding acid may be used. As catalysts, inorganic salts, commonly used for the acylation of indole derivatives, preferably magnesium perchlorate, may be used.

When an acyl halide is used for the diacylation, the reaction is carried out in an apolar aprotic solvent commonly used for the acylation with acyl halides. Suitable apolar aprotic solvents are e.g. chlorinated hydrocarbons such as chloroform, carbon tetrachloride or dichloromethane; aromatic hydrocarbons such as benzene or toluene. Preferably dichloromethane is used. This reaction is accomplished at a temperature between room temperature and the boiling point of the solvent used, preferably at room temperature.

As acid binding agent a base, e.g. sodium hydroxide, potassium hydroxide, diethylamine or triethylamine, preferably potassium hydroxide, is used. Suitable catalysts are the tetraalkylammonium salts, preferably tetrabutylammonium hydrogen sulfate.

The diacylation using ketene is carried out in a known manner, e.g. as described in Helv. Chim. Acta 40, 1706 (1957).

According to the variant (ii) of the process (b) a 2-halogenated lysergol or 2-halogenated elymoclavine, respectively, of the formula (II) is monoacylated in the 8-position by using a carboxylic acid or a carboxylic acid derivative suitable for acylation and after isolating, the thus-obtained monoacyl derivative of the formula (I), wherein R stands for hydrogen, is transformed to a diacyl derivative of the formula (I) by acylating with a carboxylic acid derivative or to a compound of the formula (I) containing a formyl group as R, by using a formylating agent.

On using a carboxylic acid, the monoacylation is accomplished in a known manner, in an apolar aprotic solvent or in an excess of the acid used, at a temperature between room temperature and the boiling point of the solvent involved in the presence of a chemical water-binding agent, preferably in the presence of dicyclohexylcarbodiimide; or by displacing the chemical equilibrium in a known manner, e.g. by azeotropic distillation.

As reactive carboxylic acid derivative, an acid anhydride or acyl halide may be used for the monoacylation. On using an acid anhydride for the monoacylation, the reaction is carried out at room temperature without any catalyst, in one of the solvents used for the above diacylations.

On using an acyl halide for the monoacylation, the reaction is similarly accomplished at room temperature, without any catalyst, in one of the solvents used in the diacylation reactions with an acyl halide.

A compound of the formula (I) containing hydrogen as R is reacted with a formylating agent, in order to be transformed to the corresponding compound of the formula (I) containing the formyl group as R. This transformation can be carried out in a known manner, preferably by using Vilsmeier's formylation method according to which a formamide derivative such as N-methylformanilide or dimethylformamide and phosgene or phosphorus oxychloride, preferably dimethylformamide and phosphorus oxychloride, are employed. An apolar aprotic solvent such as benzene or chlorobenzene or preferably, an excess of dimethylformamide may be used as solvent for this reaction. The suitable temperature of the reaction is from 60° C. up to 80° C.

According to the variant (i) of the process (c) of the invention, the starting 2-halogenated lysergol or 2-halogenated elymoclavine, respectively, of the formula (II) is formylated and halogenated simultaneously in the same step. In this case, the hydroxymethyl group in the 8-position is converted to a chloromethyl group, whereas a formyl group is bound in the 1-position.

This reaction is accomplished with a mixture of dimethylformamide and phosphorus oxychloride in a dipolar aprotic solvent commonly used for formylation, preferably in dimethylformamide itself, at a temperature between room temperature and the boiling point of the solvent used, preferably by heating for several hours.

According to the variant (ii) of the process (c), the starting 2-halogenated lysergol or 2-halogenated elymoclavine, respectively, of the formula (II) is halogenated in a known manner, e.g. as described in Coll. Czech.

Chem. Comm. 39, 2819 (1969). The starting material is dissolved in an aprotic solvent such as acetonitrile or tetrahydrofuran and treated with a halogen-containing phosphorus compound, e.g. with phosphorus pentachloride, phosphorus oxychloride or phosphorus tribromide, at a temperature between room temperature and the boiling point of the solvent used. After completion of the reaction, the thus-obtained compound of the formula (I) containing hydrogen as R and a halogen such as chlorine, bromine or iodine as R" is isolated and then formylated without purification. The formylation is carried out as described at the variant (ii) of the process (c).

The compounds of the formula (I) obtained by using any of the processes (a), (b), (c) or (d) of the invention may be isolated in such a way that the catalyst is filtered off from the reaction mixture, the thus-obtained solution is evaporated and the residue is mixed with a water-immiscible organic solvent, e.g. dichloromethane, chloroform, dichloroethane, benzene or toluene, made alkaline, if desired, by adding a 5% aqueous sodium carbonate solution, separated, washed with water, dried and evaporated. If desired, the crude product obtained as an evaporation residue is purified by recrystallization.

If desired, the compounds of the formula (I) obtained in any one step of the processes (a), (b), (c) or (d) of the invention may be converted to their acid addition salts. The acid addition salt formation can be performed in an inert solvent, e.g. in a $C_{1-6}$ aliphatic alcohol or in a dipolar aprotic solvent, e.g. in ether or acetone in such a manner that the compound of the formula (I) is dissolved in the solvent and the appropriate acid or a solution of this acid in the same solvent is added to the above solution until the pH value of the mixture becomes mildly acidic. Thereupon, the precipitated acid addition salt is separated from the reaction mixture in a suitable manner, e.g. by filtration.

The active ingredients of the formula (I) can be converted into pharmaceutical compositions by mixing them with the usual non-toxic, inert, solid or liquid carriers and/or auxiliary agents which are commonly used in compositions for enteral or parenteral administration. As carriers e.g. water, gelatine, lactose, starch, pectin, magnesium stearate, stearic acid and vegetable oils such as peanut oil or olive oil, or the like can be employed. The active ingredient can be formulated to the usual pharmaceutical compositions, particularly to solid forms such as rounded or angled tablets, dragées, capsules, e.g. gelatine capsules, pills, suppositories or the like. The amount of the solid materials can vary between wide limits, preferably they are used in an amount between about 25 mg and 1 g. The compositions may optionally contain the commonly used pharmaceutical additives, e.g. preserving agents, stabilizers, wetting agents, emulsifying agents or the like.

Particularly in the case of solid compositions, the pharmaceutical compositions can be prepared by using the common methods involving e.g. sieving, mixing, granulating and compressing the components (ingredients). The compositions may be subjected to further operations (e.g. sterilization) commonly used in the pharmaceutical industry.

On using the pharmaceutical composition, the patient is treated with a dose needed to ensure the desired effect. This dose depends upon several factors like the severity of the disease, the body-weight of the patient and the route of administration. The dose to be used is in every case to be defined by the physician.

In general, the pharmaceutical compositions according to the invention contain the active ingredient of the invention in an effective dose of 0.001 up to 100 mg/kg of body-weight. However, the quantity of the active ingredient may be, of course, more or less than the above-defined limits.

The invention also relates to a method for treating psychiatraic diseases. This process comprises administering a therapeutically effective amount of an active ingredient of the formula (I) to the patient.

The invention is illustrated in detail by the aid of the following non-limiting Examples.

Example 1

Preparation of 2-chloroelymoclavine (2-chloro-8-hydroxymethyl-6-methyl-8-ergolene)

10 g of elymoclavine are suspended in 1500 ml of tetrahydrofuran and dissolved at 60° C. under stirring. The insoluble part is filtered off, the solution is cooled to room temperature and tertiary-butyl hypochlorite solution is added in an equimolar amount. After stirring for 20 minutes, the reaction mixture is evaporated to dryness under reduced pressure and the residue is purified by chromatography on a Kieselgel column. As eluant, a 8:2 mixture of chloroform and methanol is used to give the named product in a yield of 7.9 g (70%), m.p.: 199° C.

$^1$H-NMR (CDCl$_3$+DMSO-d$_6$, δppm): 2.45 (s, 3H; N—CH$_3$); 3.95 (s, 2H; —CH$_2$OH); 6.24 (s, 1H; olefinic); 6.89 (s, 3H; aromatic).

Example 2

Preparation of 2-bromo-elymoclavine (2-bromo-8-hydroxymethyl-6-methyl-8-ergolene)

3 g of anhydrous elymoclavine are dissolved in 500 ml of anhydrous dioxane at 60° C. and 2.5 g of N-bromosuccinimide dissolved in dioxane are added dropwise to this solution under constant stirring. The mixture is stirred at 60° C. for 30 minutes, then made alkaline by adding triethylamine up to a pH value of 8 and evaporated under reduced pressure. The product is isolated by chromatography on a Kieselgel 60 column by using a 8:2 mixture of chloroform and methanol as eluant. The thus-obtained product is recrystallized from acetone to give the named compound in a yield of 2.4 g (60%), m.p.: 216° C.

Example 3

Preparation of 2-iodoelymoclavine (8-hydroxymethyl-2-iodo-2-iodo-6-methyl-8-ergolene)

3 g of anhydrous elymoclavine are dissolved in 500 ml of anhydrous dixoane at 60° C. and 3.0 g of N-iodosuccinimide dissolved in 90 ml of abs. dioxane are added dropwise to this solution under constant stirring. The mixture is stirred at 60° C. for 30 minutes, then made alkaline by adding triethylamine to a pH value of 8 and evaporated under reduced pressure. The product is isolated by chromatography on a Kieselgel 60 column by using a 8:2 mixture of chloroform and methanol as eluant. The thus-obtained product is recrystallized to give the named compound in a yield of 2.0 g (45%).

Example 4

Preparation of 2-chlorolysergol (2-chloro-8-hydroxymethyl-6-methyl-9-ergolene)

The solution of 1 g of lysergol in 40 ml of anhydrous dimethylsulfoxide is saturated with dry gaseous hydrogen chloride while keeping the temperature of the mixture below 30° C. The course of the reaction is followed by using thin layer chromatography. After the full consumption of the starting material the dimethylsulfoxide solution containing hydrogen chloride is poured into 200 ml of ice-water and the pH value is adjusted to 7 by adding aqueous ammonia. The precipitate is filtered off, dried under vacuum and, if necessary, purified by chromatography on a Kieselgel 60 column by using a 8:2 mixture of chloroform and methanol as eluant to give the named compound in a yield of 1 g (60%), m.p.: 207° C.

$^1$H-NMR (CDCl$_3$+DMSO-d$_6$, δ, ppm): 2.45 (s, 3H, N—CH$_3$); 3.55 (d; 2H; —CH$_2$OH); 6.25 (s, 1H; olefinic); 6.97 (s, 3H; aromatic).

IR (KBr), cm$^{-1}$: 3160 (indole-NH); 780 (aromatic halogen).

Example 5

Preparation of 2-chlorolysergol (2-chloro-8-hydroxymethyl-6-methyl-9-ergolene)

1 g of 2-chloroelymoclavine and 10 g of aluminium oxide (Brockman I activity) are suspended in 70 ml of toluene. The mixture is boiled under reflux for 15 minutes, then cooled to room temperature and the aluminium oxide is filtered off. The separated catalyst is mixed at 40° to 50° C. 3 times with 50 ml of methanol each and filtered off.

The combined organic phase is evaporated under vacuum. The physical characteristics of the thus-obtained named product are in complete agreement with the characteristics of the substance obtained in Example 4.

Example 6

Preparation of 2-bromolysergol (2-bromo-8-hydroxymethyl-6-methyl-9-ergolene)

Dry gaseous hydrogen bromide is introduced into 100 ml of anhydrous dimethylsulfoxide at room temperature. The quantity of the introduced hydrogen bromide gas is measured by titrating with 0.1N sodium hydroxide solution. The hydrogen bromide is introduced until the concentration of the gas reaches 0.0003–0.0005 mole/ml. One g (0.003937 mole) of lysergol is dissolved in an aliquot amount of this hydrogen bromide-dimethylsulfoxide mixture which contains 12 equivalents of hydrogen bromide. After complete dissolution, this mixture is stirred at room temperature for 20 minutes, then poured into a 5-fold volume of ice-water. Thereafter, the solution is made alkaline by adding aqueous ammonia up to a pH value of 8.9, the precipitate is filtered off, washed with water, dried and purified on a Kieselgel column by using an 8:2 mixture of chloroform and methanol to give the named compound in a yield of 0.76 g (0.00228 mole, 58%), m.p.: 193° C.

UV (methanol), τ$_{max}$=310 nm.

$^1$H-NMR (DMSO+CDCl$_3$, δ ppm): 2.48 (s, 3H; N—CH$_3$); 3.60 (d, 2H; CH$_2$—OH); 6.30 (s, 1H; olefinic); 6.95 (s, 3H; aromatic).

IR (KBr), cm$^{-1}$: 3160 (indole-NH); 780 (aromatic def.).

Example 7

Preparation of 2-bromo-elymoclavine (2-bromo-8-hydroxymethyl-6-methyl-8-ergolene)

Starting from 1 g of elymoclavine, the process described in Example 6 is followed to give the title compound in a yield of 0.7 g (55%), m.p.: 216° C.

Example 8

Preparation of 2-chloroelymoclavine (2-chloro-8-hydroxymethyl-6-methyl-8-ergolene)

The process described in Example 6 is followed, except that instead of hydrogen bromide, dry gaseous hydrogen chloride is introduced into the anhydrous dimethylsulfoxide. On using 1 g of elymoclavine as starting material, the named compound is obtained in a yield of 0.61 g (53.8%), m.p.: 199° C.

Example 9

Preparation of 2-chloro-1-methyllysergol maleate (2-chloro-1,6-dimethyl-8-hydroxymethyl-9-argolene maleate)

A suspension of 0.8 g of finely powdered potassium hydroxide in 6 ml of dimethylsulfoxide is stirred for 10 minutes, then 1 g of 2-chlorolysergol is added. The reaction mixture is stirred at 15° to 20° C. for 45 minutes, then 0.25 ml of methyl iodide is added and the mixture is stirred at 25° to 30° C. for additional 45 minutes. Thereafter, the mixture is poured into 150 ml of ice-water, the precipitate is filtered off, washed 3 times with 10 ml of water each and dried. The thus-obtained product is chromatographed on a column containing a 15-fold amount of Kieselgel by using an 8:2 mixture of chloroform and methanol as eluant. The maleate of the named base is precipitated from methanol by adding maleic acid and obtained in a yield of 0.64 g (0.0015 mole, 44%), m.p.: 205°–209° C.

$^1$H-NMR (DMSO-d$_6$, δ ppm): 3.05 (br, 3H; N—CH$_3$; 3.55 (br, 2H; CH$_2$OH); 3.72 (br, 3H; indole N—CH$_3$); 6.07 (br, 2H; olefinic, maleic acid); 6.58 (br, 1H; olefinic); 7.21 (m, 3H; indole).

IR (KBr), cm$^{-1}$: 3550–3100 (OH); 2800–2600 (protonated nitrogen); 1700–1530 (CO); 1582 (aromatic skeleton); 783 (aromatic def.).

Example 10

Preparation of 2-chloro-1-methylelymoclavine (2-chloro-1,6-di-methyl-8-hydroxymethyl-8-ergolene)

1 g of 2-chloroelymoclavine is methylated and the thus-obtained base is isolated according to the process of Example 9 to give the named compound in a yield of 0.53 g (0.00175 mole, 50.4%), m.p.: 186°–189° C.

$^1$H-NMR (DMSO-d$_6$, δ ppm): 2.31 (s, 3H; N—CH$_3$); 3.63 (s, 3H; indole N—CH$_3$); 3.98 (s, 2H; CH$_2$OH); 6.29 (s, 1H; olefinic); 7.15 (m, 3H; aromatic).

IR (KBr), cm$^{-1}$: 2820 (indole N—CH$_3$); 1607 (aromatic skeleton); 780 (aromatic def.).

Example 11

Preparation of 1-acetyl-8-acetyloxymethyl-2-chloro-6-methyl-8-ergolene 4.8 g of powdered potassium hydroxide, 1.28 g of tetrabutylammonium sulfate and 6.6 ml of acetyl chloride are added under stirring to a solution containing 1.6 g of 2-chloroelymoclavine in 200 ml of anhydrous dichloromethane. The mixture is stirred at room temperature for 3 hours. The insoluble parts are filtered off from the reaction mixture, the dichloromethane solution is extracted twice with 60 ml of saturated sodium hydrogen carbonate solution each, dried over anhydrous sodium sulfate, filtered and evaporated. The title compound is isolated on a Kieselgel column by using a 7:3 mixture of benzene and acetone as eluant (the R$_f$ value of the title compound is 0.34). The oily product obtained by the column chromatography is recrystallized from ethyl ether to give the named compound in a yield of 1.4 g (0.00376 mole, 67%), m.p.: 105°–107° C.

$^1$H-NMR (CDCl$_3$, δ ppm): 2.05 (s, 3H; O—CCH$_3$); 2.45 (s, 3H; N—CH$_3$); 2.71 (s, 3H; CCH$_3$); 4.55 (s, 2H; CH$_2$); 7.21 (m, 3H; aromatic);

IR (KBr), cm$^{-1}$: 2780 (aliphatic next to N); 1726 (ester-CO); 1690 (acid amide-CO); 1257 (ester-C-O-C); 1590–1573 (aromatic nucleus); 780 (aromatic def.).

Example 12

Preparation of 1-acetyl-8-acetyloxymethyl-2-chloro-6-methyl-9-ergolene

According to the process described in Example 11, 2.05 g of 2-chlorolysergol are acylated, isolated and the thus-obtained product is recrystallized from ethyl ether to give the named compound in a yield of 1.8 g (0.00493 mole, 71%), m.p.: 104°–107° C.

$^1$H-NMR (CDCl$_3$, δ ppm): 2.1 (s, 3H; O—CCH$_3$); 2.55 (s, 3H; N—CH$_3$); 2.71 (s, 3H; CCH$_3$); 4.05 (s, 2H; CH$_2$); 6.41 (s, 1H; olefinic); 7.11 (m, 3H; aromatic).

IR (KBr), cm$^{-1}$: 2780 (aliphatic next to N); 1730 (ester-CO); 1690 (acid amide-CO); 1263 (ester-C-O-C); 1600–1575 (aromatic nucleus); 780 (aromatic def.).

Example 13

Preparation of 1-acetyl-8-acetyloxymethyl-2-bromo-6-methyl-8-ergolene 2.0 g of 2-bromoelymoclavine are acylated and then isolated as described in Example 11. The thus-obtained product is recrystallized from ethyl ether to give the named compound in a yield of 1.4 g (0.003365 mole, 56%), m.p.: 122°–128° C.

$^1$H-NMR (CDCl$_3$, δ ppm): 2.1 (s, 3H; O—CCH$_3$); 2.55 (s, 3H; N—CH$_3$); 2.30 (s, 3H; CCH$_3$); 4.60 (s, 2H; CH$_2$); 7.3 (m, 3H; aromatic).

IR (KBr); cm$^{-1}$: 2780 (aliphatic next to N); 1726 (ester-CO); 1690 (acid amide-CO); 1257 (ester-C-O-C); 1600–1570 (aromatic nucleus).

Example 14

Preparation of 1-acetyl-8-acetyloxymethyl-2-bromo-6-methyl-9-ergolene 2.0 g of 2-bromolysergol are acylated and then isolated as described in Example 11. The thus-obtained product is recrystallized from ethyl ether to give the named compound in a yield of 1.6 g (0.003846 mole, 64%).

$^1$H-NMR (CDCl$_3$, δ ppm): 2.15 (s, 3H; O—CCH$_3$); 2.6 (s, 3H; N—CH$_3$); 2.8 (s, 3H; CCH$_3$); 4.1 (s, 2H; CH$_2$); 6.51 (s, 1H; olefinic); 7.2 (m, 3H; aromatic).

IR (KBr), cm$^{-1}$: 2780 (aliphatic next to N); 1730 (ester-CO); 1690 (acid amide-CO); 1260 (ester-C-O-C); 1600–1570 (aroomatic nucleus).

Example 15

Preparation of 8-acetyloxymethyl-2-chloro-1-formyl-6-methyl-9-ergolene sulfate 5 ml of acetic anhydride are added to a solution of 2 g of 2-chlorolysergol in 15 ml of glacial acetic acid. The homogeneous solution is stirred at room temperature for 2 hours. After completion of the reaction, the mixture is poured into 200 ml of ice-water, made alkaline to a pH value of 8 by adding aqueous ammonia and then extracted 3 times with 40 ml of chloroform each. The combined organic phase is dried over anhydrous sodium sulfate, filtered and evaporated under reduced pressure.

The residue is dissolved in 30 ml of anhydrous dimethylformamide and an equivalent amount of phosphorus oxychloride (3.4 ml) as calculated for the starting material, is added. The solution is stirred at 60° C. for 10 hours. After the termination of the formylation the reaction mixture is cooled down, poured into 250 ml of ice-water, made alkaline up to a pH value of 7.5 by adding aqueous ammonia and then extracted 3 times with 20 ml of chloroform each.

The combined organic phase is washed with 20 ml of water, dried over anhydrous sodium sulfate, filtered and evaporated under reduced pressure. The oily residue is dissolved in 10 ml of dichloromethane and chromatographed on a column prepared from 10 g of Kieselgel by using dichloromethane as eluant. The eluate is evaporated under reduced pressure and the thus-obtained product is recrystallized from acetone to give the free base corresponding to the named compound in a yield of 1.43 g, m.p.: 148°–151° C.

The thus-isolated free base is dissolved in 15 ml of methyl ethyl ketone and a solution of sulfuric acid in methyl ethyl ketone is added dropwise thereto under stirring up to a pH value of 6.5. The sulfate salt immediately starts to precipitate. The separated salt is filtered off, washed twice with 10 ml of methyl ethyl ketone and dried to give the sulfate salt in a yield of 1.56 g (0.004335 mole, 62% as calculated for 2-chlorolysergol), m.p.: 144°–145° C.

$^1$H-NMR (D$_2$O, δ ppm): 2.25 (s, 3H; 0—CH$_3$); 3.35 (s, 3H; N—CH$_3$); 4.6 (m, 2H; CH$_2$); 6.5 (s, 1H; olefinic); 7.3 (m, 3H; aromatic); 8.9 (br, 1H; formyl).

IR (KBr), cm$^{-1}$: 1730 (ester-CO); 1690 (acid amide-CO); 1260 (ester C-O-C); 1600–1575 (aromatic nucleus).

Example 16

Preparation of 2-chloro-8-chloromethyl-1-formyl-6-methyl-9-ergolene 7 equivalents (3.4 ml) of phosphorus oxychloride are added to a solution containing 2 g of 2-chlorolysergol in 30 ml of anhydrous dimethylformamide, then the solution is stirred at 60° C. for 10 hours. After completion of the reaction, the mixture is poured into 250 ml of ice-water, made alkaline up to a pH value of 7.5 by adding aqueous ammonia and extracted 3 times with 20 ml of chloroform each. The combined organic phase is washed with 20 ml of water, dried over anhydrous sodium sulfate and evaporated under reduced pressure. The residue is dissolved in 10 ml of dichloromethane and chromatographed on a column prepared from 10 g of Kieselgel by using a 95:5 mixture of chloroform and methanol as eluant. The eluate is evaporated under reduced pressure and the residue is recrystallized from methyl ethyl ketone to give the named product in a yield of 1.6 g (0.00479 mole, 69.2%), m.p.: 159°–160° C.

$^1$H-NMR (CDCl$_3$, δ ppm): 2.64 (s, 3H; N—CH$_3$); 3.65 (m, 2H; CH$_2$); 6.47 (s, 1H; olefinic); 7.2–8.4 (m, 3H; aromatic); 9.52 (s, 1H; formyl).

IR (KBr), cm$^{-1}$: 1680 (acid amide-CO); 1600–1575 (aromatic nucleus).

We claim:

1. A compound of the Formula (I)

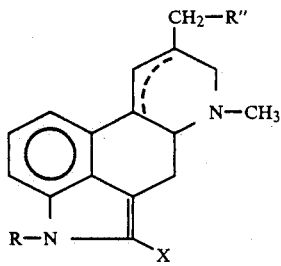

wherein
X is chloro, bromo or iodo;
R is $C_1$ to $C_4$ alkyl; and
R" is hydroxyl; or
R and R' are identical and are each $C_1$ to $C_6$ alkanoyl, benzoyl, naphthoyl, phenylacetyl, 3-phenylpropionyl, picoloyl, furoyl, nicotinoyl, isonicotinoyl, trimethoxybenzoyl, 4-chlorobenzoyl, 2-chlorobenzoyl, or pyroglutamyl; and
R" is halogen or an —OR' group; or
R is formyl;
R" is is an —OR' group; and
R' is as defined above; and the dotted lines indicate a double bond between the 8-9 or 9-10 positions; or a pharmaceutically acceptable acid addition salt thereof.

2. The compound of the Formula (I) defined in claim 1 wherein R and R' are identical and R" is —OR'; or a pharmaceutically acceptable acid addition salt thereof.

3. The compound of the Formula (I) defined in claim 1 which is 1-acetyl-8-acetoxymethyl-2-chloro-6-methyl-9-ergolene or a pharmaceutically acceptable acid addition salt thereof.

4. The compound of the Formula (I) defined in claim 1 which is 8-acetoxymethyl-2-chloro-1-formyl-6-methyl-9-ergolene or a pharmaceutically acceptable acid addition salt thereof.

5. A neuroleptic pharmaceutical composition which comprises as active ingredient a therapeutically effective amount of the compound of the Formula (I) as defined in claim 1 or a pharmaceutically acceptable acid addition salt thereof, in admixture with a pharmaceutically acceptable inert carrier.

6. A method of treating a patient with a psychiatric disease responsive to a dopaminergic antagonistic effect which comprises the step of administering to said patient a therapeutically effective amount of the compound of the Formula (I) as defined in claim 1 or a pharmaceutically acceptable acid addition salt thereof.

* * * * *